United States Patent
Lim et al.

(10) Patent No.: US 9,790,170 B2
(45) Date of Patent: Oct. 17, 2017

(54) METHOD FOR PREPARING LACOSAMIDE

(71) Applicant: ST PHARM CO., LTD., Gyeonggi-do (KR)

(72) Inventors: Geun Jho Lim, Seoul (KR); Sun Ki Chang, Gyeonggi-do (KR); Jae Hun Kim, Seoul (KR); Jong Moon Park, Gyeonggi-do (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 0 days.

(21) Appl. No.: 15/034,536

(22) PCT Filed: Oct. 27, 2014

(86) PCT No.: PCT/KR2014/010140
§ 371 (c)(1),
(2) Date: Aug. 5, 2016

(87) PCT Pub. No.: WO2015/068977
PCT Pub. Date: May 14, 2015

(65) Prior Publication Data
US 2016/0332958 A1 Nov. 17, 2016

(30) Foreign Application Priority Data

Nov. 8, 2013 (KR) .................. 10-2013-0135168

(51) Int. Cl.
*C07C 231/12* (2006.01)
*C07C 231/02* (2006.01)
*B01J 23/04* (2006.01)

(52) U.S. Cl.
CPC ............. *C07C 231/12* (2013.01); *B01J 23/04* (2013.01); *C07C 231/02* (2013.01)

(58) Field of Classification Search
None
See application file for complete search history.

(56) References Cited

U.S. PATENT DOCUMENTS

| 5,773,475 A | 6/1998 | Kohn et al. .................. 514/616 |
| 2011/0130350 A1 | 6/2011 | Riedner et al. ............... 564/136 |
| 2012/0209022 A1 | 8/2012 | Pandey et al. .................. 560/24 |
| 2013/0035508 A1 | 2/2013 | Muddasani et al. .......... 564/158 |
| 2013/0041180 A1 | 2/2013 | Reddy et al. ................. 564/158 |

FOREIGN PATENT DOCUMENTS

| WO | WO 2006/037574 | | 4/2006 |
| WO | WO 2011/039781 | | 4/2011 |
| WO | WO 2011/099033 | * | 8/2011 |
| WO | WO 2011/130615 | | 10/2011 |
| WO | WO 2012/065891 | * | 5/2012 |
| WO | WO 2012/140507 | * | 10/2012 |

OTHER PUBLICATIONS

Kirihata ("Synthesis and Structural Confirmation of (2S,3R,4R,6E)-2-Acetylamino-3-hydroxy-4-methyl-6-octenoic Acid, a New Amino Acid Produced by Neocosmospora vasinfecta" Biosci. Biotech. Biochem 59, 12, 2228-2230, 1995).*
Letter/Written Disclosure of the Information Disclosure Statement for the above-referenced application, filed herewith on Jul. 28, 2016, 2 pages.
English translation of International Search Report and Written Opinion, dated Dec. 16, 2014, in connection with International Patent Application No. PCT/KR2014/010140, 9 pages.

* cited by examiner

*Primary Examiner* — Jafar Parsa
*Assistant Examiner* — Amy C Bonaparte
(74) *Attorney, Agent, or Firm* — Dentons US LLP; Stephanie Seidman

(57) ABSTRACT

The present invention provides a novel method for preparing lacosamide with high chiral purity from D-serine. The method of the present invention can obtain lacosamide with high chiral purity in a high yield through a simple and environmentally-friendly process and thus can be easily applied to mass production.

12 Claims, No Drawings

METHOD FOR PREPARING LACOSAMIDE

TECHNICAL FIELD

The present invention relates to a novel method for preparing lacosamide. More particularly, the present invention relates to a method for preparing lacosamide with high chiral purity through a simple process and in an environmentally-friendly way.

BACKGROUND ART

Lacosamide is an amino acid derivative having analgesic and anticonvulsant properties and was first reported in U.S. Pat. No. 5,773,475. According to this literature, D-serine is reacted with acetic anhydride to produce an intermediate of an N-acetyl derivative, and this intermediate is reacted with benzylamine to produce a benzylamide derivative. Then, the benzylamide derivative is O-methylated with silver (I) oxide and methyl iodide to prepare lacosamide. However, this method results in low yield, causes partial racemization in the O-methylation process, uses expensive silver (I) oxide, and thus is not suitable for mass production and industrial use.

According to the method disclosed in WO2006037574, D-serine is N-protected with a Boc (tert-butoxycarbonyl) group, followed by O-methylation. The resulting compound is reacted with benzylamine to form an amide compound, followed by N-deprotection of the Boc group and acetylation to give lacosamide. However, this reaction involves the simultaneous use of organic solvent and water, which are not well mixed, in the O-methylation process and thus requires the use of a phase transfer catalyst for efficient reaction and the use of expensive organolithium compounds. Moreover, the reaction involves the N-protection and N-deprotection of the Boc group, which prolongs the process.

In addition, according to the methods for preparing lacosamide developed so far, in order to minimize the occurrence of racemization in the O-methylation process, sterically hindered protecting groups were used for the amine of D-serine and were subjected to deprotection, and thus the preparation of lacosamide requires many processes.

Therefore, there is a need to develop a method for preparing lacosamide in a simpler, more economic and environmentally-friendly way.

DISCLOSURE

Technical Problem

An object of the present invention is to provide an economic and environmentally-friendly method for preparing lacosamide with high chiral purity through a simple process.

Technical Solution

The present invention provides a method for preparing lacosamide represented by Formula 1, the method comprising: preparing a compound represented by Formula 3 by reacting a compound represented by Formula 2 with a methylating agent in the presence of an inorganic lithium compound:

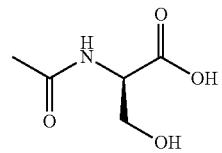

[Formula 2]

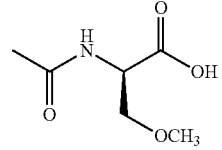

[Formula 3]

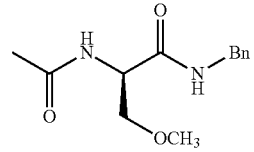

[Formula 1]

wherein in Formula 1, Bn represents a benzyl group.

The method for preparing lacosamide of the present invention can prepare lacosamide with high purity using an environmentally-friendly solvent without the use of a phase transfer catalyst or other expensive materials through a simple process in a high yield and thus can be easily applied to mass production.

In the present invention, the compound represented by Formula 3 may be prepared by using water only as a solvent. For example, the compound represented by Formula 3 may be prepared by adding the inorganic lithium compound to an aqueous solution containing the compound represented by Formula 2 and then adding the methylating agent thereto. The addition of the inorganic lithium compound may be the addition of an aqueous solution containing the inorganic lithium compound.

In the preparation of the compound of Formula 3, the present invention does not use any organic solvent other than water, which does not require the use of the phase transfer catalyst, and the reaction can be carried out in an environment-friendly atmosphere.

In the present invention, the methylating agent is dimethylsulfate.

In the present invention, the methylating agent may be added in three divided portions.

In the present invention, the compound represented by Formula 2 may be prepared by reacting D-serine with acetic anhydride.

The reaction of D-serine and acetic anhydride may use a mixture of water and C1-C3 alcohol as a solvent, preferably a mixture of water and methanol.

In the present invention, the reaction of D-serine and acetic anhydride ($Ac_2O$) may be carried out in the presence of sodium hydrogen carbonate ($NaHCO_3$), potassium hydrogen carbonate ($KHCO_3$) or a mixture thereof.

In the present invention, the inorganic lithium compound acts as a base and may be lithium hydroxide (LiOH) or a hydrate thereof, preferably lithium hydroxide monohydrate.

In the present invention, the lacosamide represented by Formula 1 may be prepared by reacting the compound represented by Formula 3 with benzylamine ($BnNH_2$) in the presence of isobutylchloroformate (IBC) and a base.

In the present invention, the base may be a tertiary amine, preferably, 4-methylmorpholine (NMM), triethylamine, pyridine, or a mixture thereof, more preferably methylmorpholine.

In the present invention, the method of preparing the lacosamide represented by Formula 1 may comprises:

preparing a mixture by adding isobutylchloroformate and a base to the compound represented by Formula 3;

preparing a reaction solution by adding benzylamine to the mixture; and then stirring the reaction solution.

In the present invention, the preparation of the mixture and the reaction solution may be carried out at −20° C. to −5° C., preferably −15° C. to −10° C.

In the present invention, the stirring the reaction solution may be performed at a room temperature.

In the present invention, the lacosamide may be prepared by a method represented by the following reaction scheme:

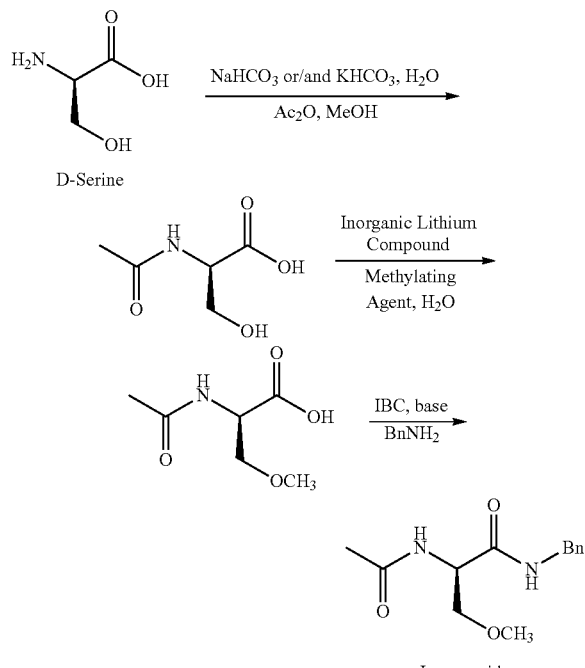

Lacosamide

Advantageous Effects

The present invention provides an environmentally-friendly and economic method for preparing lacosamide which can perform the O-methylation of D-serine with high chiral purity without the use of toxic organic solvent, catalyst, etc.

MODE FOR INVENTION

Hereinafter, preferred examples will be described for a better understanding of the present invention. However, the following examples are provided for illustrative purpose only, and are not intended to limit the scope of the present invention.

Moreover, unless otherwise states, the reagents and solvents mentioned below were purchased from Sigma-Aldrich Korea, HPLC was performed with 1200 Series (Agilent Technologies), 1H NMR was recorded on an Oxford NMR 300 MHz spectrometer (Varian Mercury Instrument). The purity and chiral purity was determined by area percentage of HPLC.

Example 1

Preparation of (R)-2-acetamido-3-hydroxypropanoic acid (the Compound Represented by Formula 2)

D-serine (5 g, 0.0476 mole) was suspended and stirred in a mixed solvent of 25 ml of methanol and 25 ml of purified water, and then sodium hydrogen carbonate (12 g, 0.1428 mole) was added at a room temperature, and acetic anhydride ($Ac_2O$, 10.8 ml, 0.114 mole) was slowly added. The resulting solution was stirred at a room temperature for 30 minutes, and after the completion of the reaction, the reaction solvent was removed by concentration under reduced pressure. Then, 20 ml of purified water was added, and a 1 N aqueous solution of hydrochloric acid was added to adjust the pH to 3. After 100 ml of ethanol was added to the concentrated residue and stirred, the resulting solid was removed by filtration, and the filtrate was concentrated to yield quantitatively (R)-2-acetamido-3-hydroxypropanoic acid as a crude acetyl-D-serine.

$^1$H-NMR (DMSO) δ (ppm) 7.37 (d, 1H) 3.75 (q, 1H) 3.50 (dd, 1H) 3.28 (dd, 1H) 1.82 (s, 3H)

Example 2

Preparation of (R)-2-acetamido-3-methoxypropanoic acid (the Compound Represented by Formula 3)

(R)-2-acetamido-3-hydroxypropanoic acid (the compound represented by Formula 2) (7 g, 0.0476 mole) was dissolved in 60 ml of purified water and cooled to 0 to 10° C. Then, a 20 wt % aqueous solution of lithium hydroxide monohydrate (10 g, 0.238 mole) was added dropwise while maintaining the temperature, and the resulting solution was stirred for 20 minutes. After dimethylsulfate (13.6 ml, 0.1428 mole) was added dropwise at the same temperature in three divided portions every 30 minutes, the resulting mixture was stirred at the same temperature for 3 hours, and then heated to room temperature (20 to 25° C.). Upon the completion of the reaction after stirring for 2 hours, the filtration was performed and then the filtrate was washed with 50 ml of methylenechloride, and the aqueous phase was separated. After the separated aqueous phase was cooled below 10° C., 3 N aqueous solution of hydrochloric acid was added to adjust the pH to 2.5 to 3, followed by concentration under a reduced pressure. The concentrated residue was suspended in 150 ml of ethyl acetate and filtered, and the filtrate was concentrated to yield the target product in the form of syrup. The yield was 84.1%.

$^1$H-NMR (DMSO) δ (ppm) 8.15 (d, 1H) 4.38 (m, 1H) 3.58~3.63 (dd, 1H) 3.45~3.49 (dd, 1H) 3.23 (s, 3H) 1.84 (s, 3H)

Example 3

Preparation of lacosamide, (R)-2-acetamido-N-benzyl-3-methoxypropionamide (the Compound Represented by Formula 1)

(R)-2-acetamido-3-methoxypropanoic acid (the compound represented by Formula 3) (13 g, 0.081 mole) was dissolved in 260 ml of tetrahydrofuran and cooled below −15° C., and isobutylchloroformate (IBC, 11.1 ml, 0.085 mole) was added and stirred for 10 minutes. 4-methylmorpholine (NMM, 9.3 ml, 0.089 mole) was added dropwise while maintaining the temperature below −10° C., and benzylamine (BnNH₂) was added at the same temperature. The resulting mixture was kept at −15° C. to −10° C. for 1 hour, heated to a room temperature, and then stirred for 3 hours. The reaction solvent was removed by concentration, and the extraction was performed by adding 130 mL of methylenechloride and 13 ml of purified water. The aqueous phase was re-extracted with 60 ml methylenechloride and combined with the organic phase. A separate organic phase was washed sequentially with 100 ml of a 2 wt % aqueous solution of hydrochloric acid, 100 ml of a 2 wt % aqueous solution of sodium hydrogen carbonate, and 10 wt % brine, respectively, to separate an organic phase. Then, the separate organic phase was concentrated under reduced pressure. After ethyl acetate (130 ml) was added to the concentrated residue, the concentrated residue was dissolved by heating the resulting mixture to 60° C., and normal heptane (130 ml) was slowly added. Then, the reactant was cooled to a room temperature and stirred for 2 hours, and the resulting solid was filtered and dried to yield 11 g of lacosamide (I).

Yield: 55%; purity 99.7%; and chiral purity: 100%

¹H-NMR (DMSO) δ (ppm) 8.45 (t, 1H) 8.07 (d, 1H) 7.23 (m, 5H) 4.49 (m, 1H) 4.24 (dd, 2H) 3.5 (m, 2H) 3.25 (s, 3H) 1.87 (s, 3H)

INDUSTRIAL APPLICABILITY

As described above, the present invention provides an environmentally-friendly and economic method for preparing lacosamide which can perform the O-methylation of D-serine with high chiral purity without the use of toxic organic solvent, catalyst, etc.

The invention claimed is:
1. A method for preparing lacosamide of Formula 1:

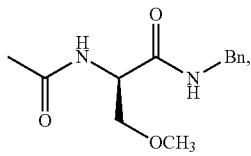

Formula 1 wherein Bn represents a benzyl group,
the method comprising:
preparing a compound of Formula 3:

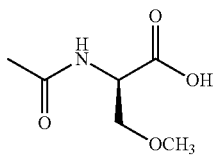

Formula 3 by reacting a compound of Formula 2:

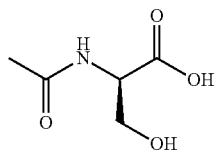

Formula 2 with a methylating agent in the presence of an inorganic lithium compound and only water as a solvent; and
preparing the lacosamide of Formula 1 by reacting the compound of Formula 3 with benzylamine.

2. The method of claim 1, wherein the preparing of the compound of Formula 3 comprises:
adding the inorganic lithium compound to an aqueous solution containing the compound of Formula 2; and
adding the methylating agent after the addition of the inorganic lithium compound.

3. The method of claim 1, wherein the methylating agent is dimethylsulfate.

4. The method of claim 1, wherein the compound of Formula 2 is prepared by reacting D-serine with acetic anhydride.

5. The method of claim 4, wherein the reacting D-serine with acetic anhydride uses a mixture of water and C1-C3 alcohol as a solvent.

6. The method of claim 4, wherein the reacting D-serine and acetic anhydride is carried out in the presence of at least one compound selected from the group consisting of sodium hydrogen carbonate and potassium hydrogen carbonate.

7. The method of claim 1, wherein the inorganic lithium compound is lithium hydroxide (LiOH) or a hydrate thereof.

8. The method of claim 1, wherein the reacting the compound of Formula 3 with benzylamine is carried out in the presence of isobutylchloroformate and a base.

9. The method of claim 1, wherein the reacting the compound of Formula 3 with benzylamine comprises:
preparing a mixture containing the compound of Formula 3, isobutylchloroformate and a base; and
preparing a reaction solution by adding benzylamine to the mixture.

10. The method of claim 9, further comprising stirring the reaction solution.

11. The method of claim 9, wherein the preparing the mixture and the reaction solution are carried out at −20° C. to −5° C.

12. The method of claim 9, wherein the base comprises at least one base selected from the group consisting of 4-methylmorpholine, triethylamine, and pyridine.

* * * * *